US00PP27140P3

(12) United States Plant Patent
Clark et al.

(10) Patent No.: US PP27,140 P3
(45) Date of Patent: Sep. 6, 2016

(54) COLEUS PLANT NAMED 'UF12-30-6'

(50) Latin Name: *Solenostemon scuttelarioides*
Varietal Denomination: UF12-30-6

(71) Applicant: Florida Foundation Seed Producers, Inc., Marianna, FL (US)

(72) Inventors: David G. Clark, Gainesville, FL (US); Grayson M. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 90 days.

(21) Appl. No.: 14/120,604

(22) Filed: Jun. 6, 2014

(65) Prior Publication Data

US 2015/0359154 P1 Dec. 10, 2015

(51) Int. Cl.
*A01H 5/12* (2006.01)

(52) U.S. Cl.
USPC ..... Plt./469

(58) Field of Classification Search
USPC ..... Plt./469, 373, 263.1
See application file for complete search history.

(56) References Cited

U.S. PATENT DOCUMENTS

| | | | |
|---|---|---|---|
| PP21,585 | P2 | 12/2010 | Clark et al. |
| PP21,602 | P2 | 12/2010 | Clark et al. |
| PP23,585 | P3 | 5/2013 | Clark et al. |
| 2015/0359156 | P1 | 12/2015 | Clark et al. |

OTHER PUBLICATIONS

Buck. University of Florida IFAS News Feb. 19, 2014. UF/IFAS approves 14 new cultivars for release, retrieved on Nov. 9, 2015, retrieved from the Internet at <https://news.ifas.ufl.edu/2014/02/ufifas-approves-14-new-cultivars-for-release/> 4 pp.*
U.S. Appl. No. 14/120,606, filed Jun. 6, 2014, Clark et al.

* cited by examiner

*Primary Examiner* — June Hwu
(74) *Attorney, Agent, or Firm* — Dentons US LLP

(57) ABSTRACT

'UF12-30-6' is a new coleus plant distinguished by having consistent chartreuse-colored leaves with excellent lateral branching and growth habit, as disclosed herein.

4 Drawing Sheets

Latin name of the genus and species of the plant claimed: *Solenostemon scutellarioides.*

Cultivar denomination: 'UF12-30-6'.

BACKGROUND OF THE INVENTION

The invention relates to a new and distinct cultivar of coleus plant named 'UF12-30-6'. 'UF12-30-6' originated from an open pollination conducted in May-November 2011 in Gainesville, Fla. between the female coleus plant 'UF11-4-13' (unpatented) and an unknown male coleus plant. The first asexual reproduction was performed in May 2012 in Gainesville, Fla. by vegetative stem cuttings using a single seedling (see FIG. 1 for pedigree).

'UF12-30-6' has been reproduced asexually for over one year through vegetative stem cuttings and has been found to retain its distinctive characteristics through successive asexual propagations.

'UF12-30-6' has not been made publicly available more than one year prior to the filing date of this application.

When 'UF12-30-6' is compared to the female parent 'UF11-4-13', 'UF12-30-6' has large, deep, chartreuse-colored leaves with no other distinguishing markings, while 'UF11-4-13' has smaller leaves colored lime green with leaf veins irregularly colored deep magenta.

When 'UF12-30-6' is compared to the commercial cultivar 'Lifelime' (unpatented), both plants have chartreuse foliage, but 'UF12-30-6' has a deeper, more vibrant color, particularly when grown in full sun, while 'Lifelime' is known to fade.

Leaves on 'UF12-30-6' are also distinguishable from those on 'Lifelime' because they remain pure in color, while 'Lifelime' leaves often have the presence of red colored imperfections due to genetic instability, likely due to epigenetics or an active transposon in 'Lifelime'. Leaves of 'Lifelime' are more rounded at the base of the leaf than 'UF12-30-6', while 'UF12-30-6' has a more pointed distal tip and more deeply lobed serration pattern along the leaf edge. Although not considered to be completely resistant, when grown in the greenhouse, 'UF12-30-6' has been observed to have more tolerance to downy mildew (*Peronospora* sp.) than 'Lifelime'. 'UF12-30-6' also has a more vigorous and more spreading growth habit with more lateral branching than 'Lifelime', thus providing more vegetative propagules for producers and more dense foliage cover for gardeners.

SUMMARY OF THE INVENTION

The following are the most outstanding and distinguishing characteristics of 'UF12-30-6' when grown under normal horticultural practices in Gainesville, Fla. 'UF12-30-6' has a novel vigorous, spreading growth habit, late season flowering, excellent heat tolerance, and consistent deep chartreuse leaves that are significantly different than other coleus plants. It has superior foliage color stability in both sun and shade conditions, maintaining consistent color in all conditions. It has a vigorous spreading growth habit with excellent lateral branching when grown as a stock plant, thus providing ample vegetative propagules.

BRIEF DESCRIPTION OF THE DRAWINGS

This new coleus plant is illustrated by the accompanying photographs, which show the plant's form and foliage. The colors shown are as true as can be reasonably obtained by conventional photographic procedures.

FIG. 2—shows the growth habit, form, and foliage of the claimed plant.

FIG. 3—shows a close-up of the foliage.

FIG. 4—shows foliage of UF12-30-6 (left) compared to 'Lifelime' (right).

DETAILED BOTANICAL DESCRIPTION

Figure 1:
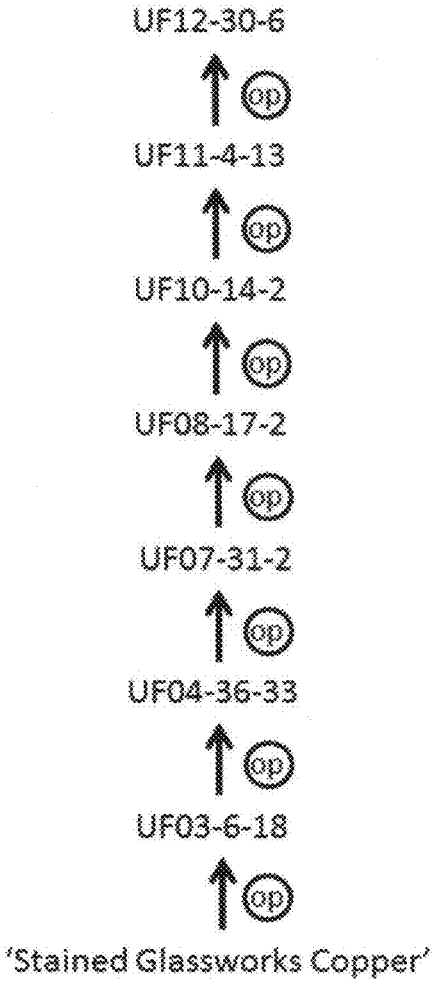
FIG. 1—shows the pedigree of the claimed plant.
Figure 2:
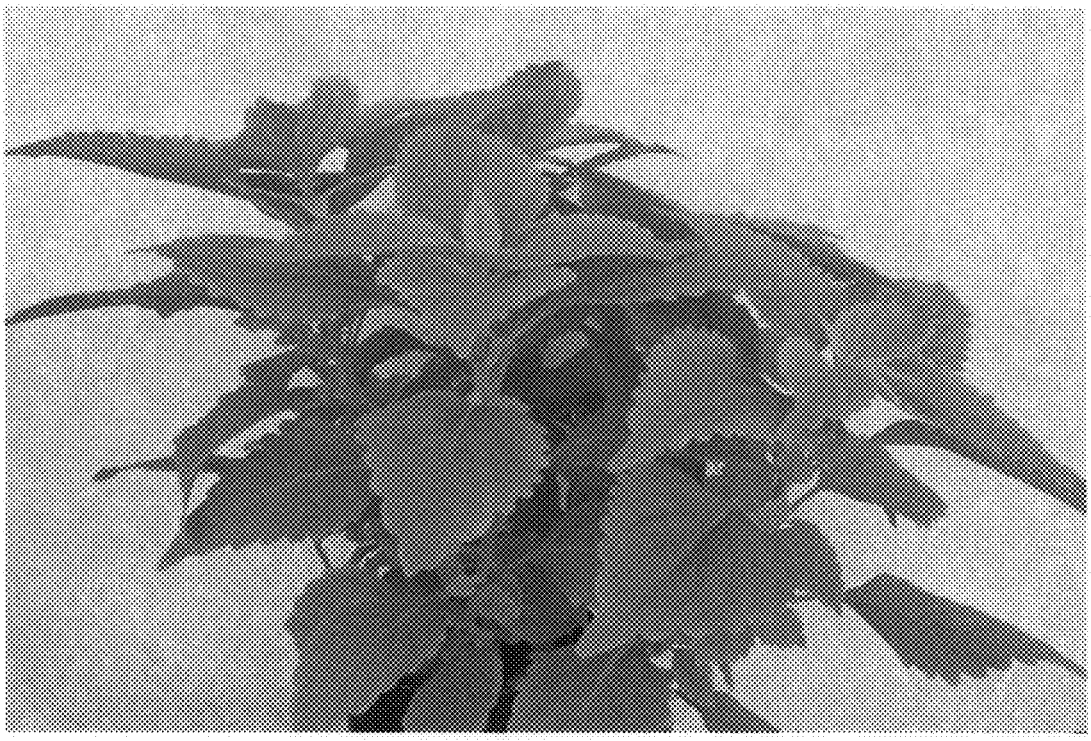
FIGS. 2 and 3 were taken of 9-week-old plants grown from cuttings in 1-gallon pots during September-November 2013 in greenhouses in Gainesville, Fla.
Figure 3:
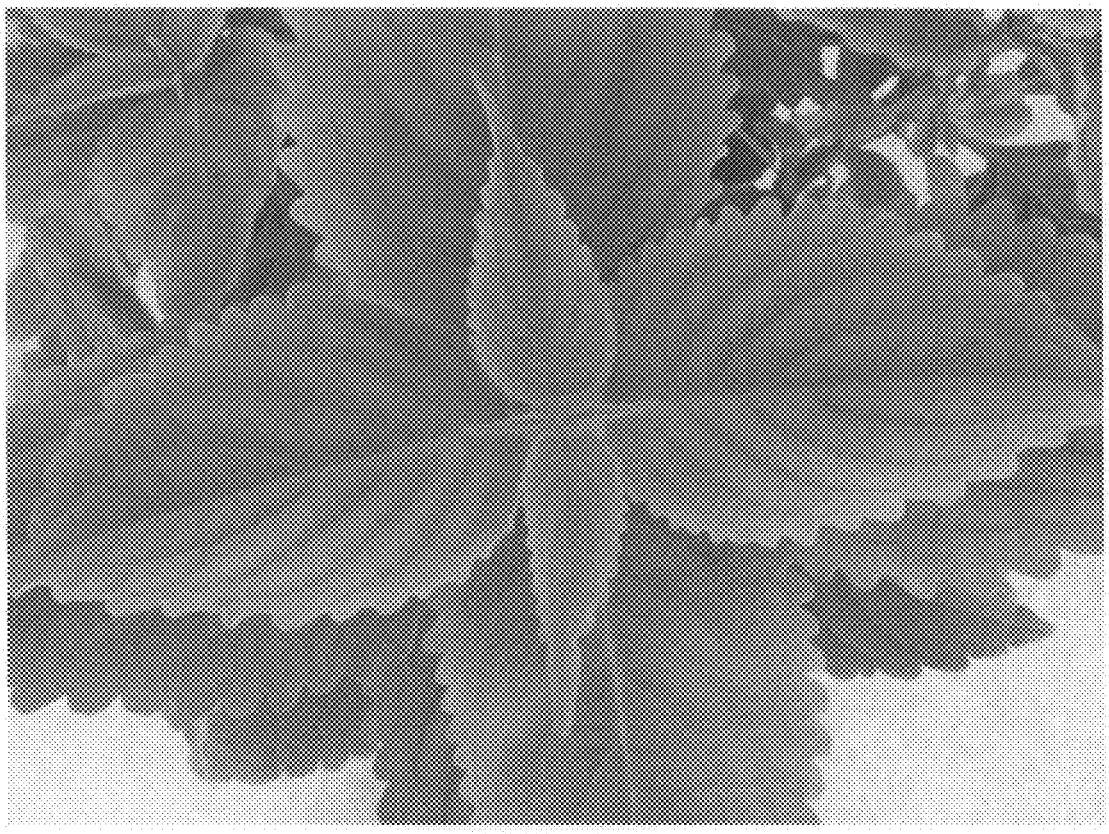
Figure 4:
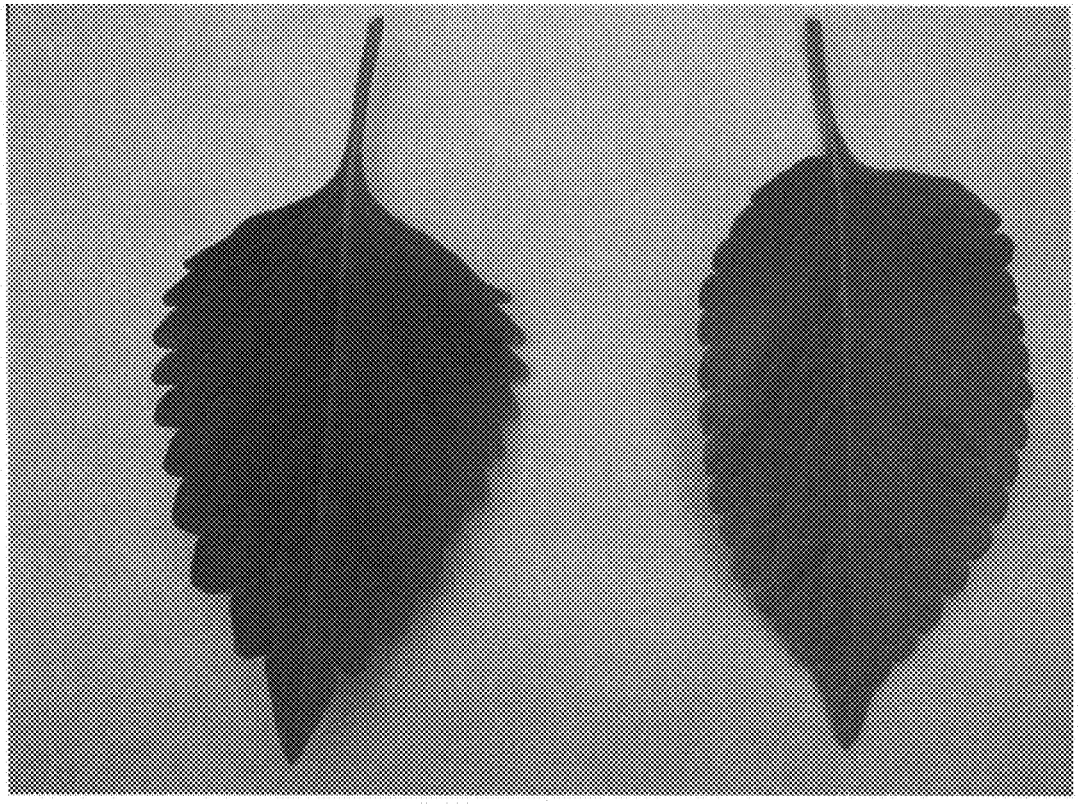
FIG. 4 was taken in May 2014 of 3-month-old stock plants at a nursery in Carleton, Mich.

The following detailed description sets forth the distinctive characteristics of coleus variety 'UF12-30-6'. The detailed description was obtained using 9-week-old plants from cuttings growing in a glass greenhouse in Gainesville, Fla. in late fall 2013. The plants were pinched 2 weeks after cuttings were rooted, then grown in 1-gallon pots for approximately 9 weeks. Color references are to The R.H.S. Colour Chart of The Royal Horticultural Society of London (R.H.S.), 2007 5th Edition.

Classification:

*Family*.—Lamiaceae.

*Botanical*.—*Solenostemon scutellarioides*.

*Common name*.—Coleus.

*Cultivar name*.—'UF12-30-6'.

Parentage:

*Female parent*.—'UF11-4-13'.

*Male parent*.—Open-pollinated.

Plant description:

*Form*.—Spreading.

*Habit*.—Upright.

*Height* (*from top of soil*).—34 cm.

*Width* (*horizontal plant diameter*).—48.5 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant*.—6 main branches per plant with numerous side branches, pinched once.

*Branch color*.—RHS 144B.

*Texture*.—Smooth.

*Pubescence*.—Non-descript.

*Stem description*.—Square-shaped stem, 1.5-2.0 cm in diameter at the soil line.

*Branch diameter*.—0.6 cm at the base of a 26-cm-long branch.

*Branch length*.—24-26 cm.

*Internode length*.—3-5 cm.

*Anthocyanin*.—N/A.

Leaves:

*Quantity of leaves per branch*.—16. Arrangement: Opposite.

*Fragrance*.—Not fragrant.

*Shape*.—Ovate.

*Length*.—11-13 cm.

*Width*.—7-9 cm.

*Apex*.—Broadly acuminate.

*Base*.—Attenuate.

*Margin*.—Sinuate.

*Leaf texture* (*both surfaces*).—Smooth, no pubescence.

*Pubescence color* (*both surfaces*).—None.

*Venation color*.—Upper surface: RHS 145C. Lower surface: RHS 145B.

*Venation pattern*.—Upper surface: Reticulate. Lower surface: Reticulate.

*Color*.—Immature leaf: Upper surface: RHS N144B. Lower surface: RHS 150B.

*Color*.—Mature leaf: Upper surface: RHS N144A. Lower surface: RHS 145A.

*Petiole length*.—3-5 cm.

*Petiole diameter*.—0.2-0.3 cm.

*Petiole color*.—RHS 144B.

*Petiole texture*.—Smooth, no pubescence.

Flowers and seeds: Flowers and seeds have not been observed.

Fruit/seed set: Fruit/seed not observed.

Disease and insect resistance: Insect resistance is typical of the species, thus no claims are made of any superior insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora* sp.), and this plant possesses better tolerance to this pathogen than other similar cultivars in the trade (e.g., 'Lifelime').

What is claimed is:

1. A new and distinct variety of *Solenostemon scutellarioides* plant called 'UF12-30-6' as shown and described herein.

* * * * *